United States Patent [19]

Scattergood et al.

[11] Patent Number: 4,894,444

[45] Date of Patent: Jan. 16, 1990

[54] RECOVERY AND PURIFICATION OF IMMUNOGENS FROM IMMUNOGEN-ALUM COMPLEXES

[75] Inventors: Edgar M. Scattergood, Lansdale, Pa.; Roy W. Grabner, Ballwin, Mo.

[73] Assignee: Merck & Co., Inc., Rahway, N.J.

[21] Appl. No.: 74,376

[22] Filed: Jul. 16, 1987

[51] Int. Cl.$^4$ .................... C07K 3/26; C07K 3/28
[52] U.S. Cl. .................... 530/414; 530/412; 530/422; 530/425
[58] Field of Search ............ 530/412, 414, 417, 415, 530/422, 423, 425, 806; 210/634, 651, 660

[56] References Cited

U.S. PATENT DOCUMENTS

| | | | |
|---|---|---|---|
| 4,340,589 | 7/1982 | Uemura et al. | 424/101 |
| 4,529,542 | 7/1985 | Umezawa et al. | 530/825 |
| 4,707,542 | 11/1987 | Friedman et al. | 435/68 |
| 4,710,387 | 12/1987 | Ohtomo et al. | 424/89 |

FOREIGN PATENT DOCUMENTS 156242 10/1985 European Pat. Off. .

OTHER PUBLICATIONS

Flaschel, E. et al. "Ultrafiltration for the Separation of Biocatalysts," In: *Advances in Biochemical Engineering/Biotechnology* (New York, Springer Verlag, 1983), pp. 73, 120, 123.
Doel and Stapel, J. Biol. Std. 10: 185, 1982.
Zatz et al., Drug. Devel. Indus. Pharm. 12:561, 1986.

*Primary Examiner*—Margaret Moskowitz
*Assistant Examiner*—Keith C. Furman
*Attorney, Agent, or Firm*—John W. Harbour; Michael C. Sudol

[57] ABSTRACT

Immunologically intact protein or peptide immunogens are recovered from vaccines consisting of immunogen-aluminum hydroxide (alum) complexes. Recovery consists of dissolution of the complexes with an alkali metal salt of a carboxylic acid at a basic pH, reduction of the pH to physiological levels, removal of excess dissolvent and isolation of the protein or peptide immunogen.

10 Claims, No Drawings

RECOVERY AND PURIFICATION OF IMMUNOGENS FROM IMMUNOGEN-ALUM COMPLEXES

BACKGROUND OF THE INVENTION

Protein or polypeptide immunogens such as hepatitis B surface antigen are formulated for human vaccine use by adsorption to aluminum hydroxide (alum). Once the protein has been insolubilized by the adsorption to alum it is impossible to further process or reprocess the immunogen without removing the alum. Dissolution of the protein-alum complex may be necessitated by compromised sterility or a requirement to re-work the vaccine. The inability to re-work or resterilize the vaccine may result in a substantial economic loss if it must be discarded. In the past, the alum was removed by treatment of the protein-alum complex with a strong acid or base capable of dissolving the alum. While the acid or base efficiently dissolved the alum, it also destroyed the immunogenicity of the protein and rendered it ineffective as a vaccine.

OBJECTS OF THE INVENTION

It is, accordingly, an object of the present invention to provide a process for removing alum from protein-alum complexes. Another object is to provide a process for removing alum from protein-alum complexes without altering the immunogenicity of the protein. Another object is to provide a process that can be scaled up for commercial recovery of protein from protein-alum complexes. A further object is to provide a process for recovery of a sterile protein immunogen from protein-alum complexes. These and other objects of the present invention will be apparent from the following description.

SUMMARY OF THE INVENTION

Immunologically intact Protein or peptide immunogens are recovered from vaccines consisting of immunogen-aluminum hydroxide (alum) complexes. Recovery consists of dissolution of the complexes with an alkali metal salt of a carboxylic acid at a basic PH, reduction of the pH to Physiological levels, removal of excess dissolvent and isolation.

DETAILED DESCRIPTION OF THE INVENTION

The present invention relates to a process for removing aluminum hydroxide (alum) from protein or peptide, hereafter referred to as protein, immunogen vaccines without altering the immunogenicity of the proteinaceous material. The process is one which can be used for samples as small as about 5 ml, and can be efficiently scaled up for commercial preparations with volumes of about 30 L or more.

Initially, alum is dissolved by treating the antigen-alum complex with either a strong acid such as about 1N HCl or a strong base such as about 1N NAOH. Acid treatment not only dissolves the alum but also renders the protein partially insoluble. Treatment with base is equally efficient in dissolving the alum but results in a significant loss of protein. Both treatments are unacceptable for reworking protein vaccines since the protein is either insoluble or has been degraded.

Alkali metal salts of mono, di, or tricarboxylic acids are used to remove alum from protein antigen-alum complexes. The carboxylic acid is acetic, citric, lactic, tartaric or gluconic while the alkali metal is lithium, sodium or potassium. The dissolvent is selected from the group consisting of: lithium, sodium or potassium acetate; sodium lactate; lithium, sodium or potassium citrate; sodium or potassium tartrate; and sodium or potassium gluconate. The preferred dissolvent is trisodium citrate, $Na_3C_6H_5O_7$.

The conditions under which sodium citrate is used to dissolve alum are critical. The addition of solid sodium citrate at a final concentration of about 2% dissolved the alum but when the protein immunogen was dialized and readsorbed to alum the relative potency of the immunogen was very low. Relative potency as used herein refers to an in vitro assay to quantitatively measure the amount of hepatitis B surface antigen on alum preparations. A known amount of experimental immunogen is reacted with radiolabeled antiserum specific for hepatitis B surface antigen using the AUSRIA-II radioimmuneassay kit (Abbott) and compared to a reference standard of known biological activity.

Dialysis of protein-alum complexes against alkali metal salts of mono, di, or tricarboxylic acids in water, about 1% to about 5% dissolves the alum and allows the recovery of the protein. The protein is, however, nonimmunogenic when readsorbed to alum as determined by the relative potency assay.

The dissolution of alum from protein-alum complexes with the protein remaining immunogenic is accomplished by direct mixing of an alkali metal salt of a mono, di or tricarboxylic acid under stringent conditions of temperature, pH and time. If the critical parameters of temperature, time and pH are not adhered to there is loss of immunogenic activity. Volumes of alum conjugated vaccine from about 5 ml to about 30 L or more are mixed with the preferred dissolvent, sodium citrate. Protein-alum complexes are treated with about equal volumes of about 1% to about 5% solution of sodium citrate in water, with about 3% being preferred. The pH of the sodium citrate solution is critical to the dissolution of an immunogenic protein and is generally between about pH 8.9 and about pH 9.5 at a temperature of between about 20° C. and about 25° C., with a pH of 9.2 being preferred. The temperature at which dissolution is carried out is also critical and both pH and temperature effect the time required for dissolution. Dissolution is carried out at temperatures between about 10° C. and about 27° C. with temperatures less than 20° C. being preferred.

Dissolution of the protein-alum complex is monitered by evaluating the pH of the dissolution solution following the combining of the sodium citrate solution and the protein-alum complex. The initial pH following combination is between about pH 7.6 and about pH 8.0. The pH of the solution increases and peaks at about pH 9.4 to about pH 9.9 with the turbid protein-alum complex becoming clear as the pH peaks. Dissolution is generally complete within about 60 minutes to about 240 minutes, with about 150 minutes being preferred. The time interval at which the protein remains at the elevated pH is extremely critical to the resulting immunogenicity of the protein. Once the maximum pH is reached the solution is allowed to remain for about 15 minutes to about 60 minutes, with 30 minutes being preferred. A quantity of about 1N HCl sufficient to reduce the pH of the protein solution to a pH of about 7.4 is added. The total time required for dissolution is about 1 hour to about 5 hours.

The processed protein is filter sterilized to remove any contaminants. Filtration is accomplished by the use of filtration membranes with a pore size of about 0.22 micron. The immunogen is concentrated by lyophilization, hydrophilic materials, pervaporation or ultrafiltration, with ultrafiltration being preferred. The sterile immunogen is preferably concentrated by membrane or hollow fiber filtration approximately 6 fold. Purification of the immunogen is carried out by filtration or dialysis to remove the sodium citrate and low molecular weight alum components. The preferred method for purification is diafiltration. The immunogen can now be reprocessed for vaccine production. Protein recovery ranges between 70% and 90%. Analytical and biological analysis of the recovered protein revealed no biochemical or biological changes as a result of the recovery process.

The following Examples illustrate the present invention without, however, limiting the same thereto.

EXAMPLE

Recovery Process

A 31.2 L volume of hepatitis B surface antigen-alum complex, pH 5.6, containing approximately 20 μg protein per ml, as determined by the Lowry Protein Assay, was solubilized by the addition of 30 L of a 3% solution of sodium citrate ($Na_3C_6H_5O_7 \cdot 2H_2O$) in water. Sodium ethylmercurithiosalicylate was added to the sodium citrate solution at a concentration of 1:20,000, the solution was adjusted to pH 9.2 and sterilized before mixing with the protein-alum complex. Dissolution was carried out at room temperature with the end point dependent upon the pH and temperature of the mixture of the protein-alum product and 3% sodium citrate. Dissolution time is adversely affected by operating at lower pH as well as colder temperatures. Dissolution is monitored by the clearing of the solution and a peaking of pH following the addition of the sodium citrate. The 30 L protein-alum batch cleared in about 1 hour at a maximum pH of 9.8.

The pH of the cleared solution was reduced to about pH 7.5 by the addition of an adequate volume of 1N HCl within one-half hour after dissolution. The solution is immediately filter sterilized with a MilliPak ® 100 cartridge, 0.22μ. Prior to reprocessing, the solubilized protein solution is concentrated to return the antigen concentration to the predissolution level. Concentration was carried out with an Amicon ® DC-2 hollow fiber unit utilizing a H1 5-20 cartridge.

Excess sodium citrate and low molecular weight alum components were removed by diafiltration. The diafiltration purification step was carried out at 4° C. and utilized 56l of dialysate (7 volumes) consisting of steril: NaCl, 8.9 g/l; $Na_2HPO_4 \cdot 12H_2O$, 1.7 g/l; $NaH_2PO_4 \cdot H_2O$, 0.2 g/L with an Amicon DC-2 hollow fiber system and 2, 2 L back washes. Use of the hollow fiber unit required back flushing to prevent loss of the protein in the fiber cartridge. The concentration of the protein can be adjusted and the material may be filter sterilized as above for reprocessing. The biologically activity of the protein immunogen was determined by the relative potency assay as described above following readsorption to alum. The relative potencies ranged from 1.31 to 1.48 and were equal to those found for non-processed immunogen. Sodium citrate derived immunogen was also assayed in a mouse potency assay. Groups of mice, 10 per group, were injected with a standard dose of the reprocessed immunogen. The mice were bled at 6 weeks post injection, the serum collected and assayed for the presence of antibody. Anti-hepatitis B surface antibody was detected using the AUSAB (Abbott) radioimmune assay and the manufacturer's procedures. The antibody levels were compared to standards. The reprocessed immunogen was as potent in the mouse system as non-reprocessed immunogen.

What is claimed is:

1. A process for recovering hepatitis B surface antigens from hepatitis B surface antigen alum complexes without altering the immunogenicity of the hepatitis B surface antigens which comprises the following steps:
   a. dissolution of the hepatitis B surface antigen alum complex by treating the complexes with a concentration of from about 1% to about 5% of an alkali metal salt of a carboxylic acid, at a pH between about 8.9 and 9.5, at a temperature of from about 10° to about 27° C., for about 60 to about 240 minutes; followed by
   b. sterilization;
   c. concentration; and
   d. purification.

2. A method according to claim 1, step a, wherein the alkali metal is selected from the group consisting of lithium, sodium and potassium.

3. A method according to claim 2 wherein the alkali metal is sodium.

4. A method according to claim 1, step a, wherein the carboxylic acid is selected from the group of acetic, citric, lactic, tartaric and gluconic acids.

5. A method according to claim 4 wherein the carboxylic acid is citric acid.

6. A method according to claim 1, step a, wherein the alkali metal salt of the carboxylic acid is sodium citrate.

7. A method according to claim 1 wherein the concentration of the alkali metal salt of the carboxylic acid is about 3%.

8. The process of claim 1, step b, wherein sterilization is accomplished by filtration.

9. The process of claim 1, step c, wherein the concentration is accomplished by ultrafiltration.

10. The process of claim 1, step d, wherein the purification is accomplished by diafiltration.

* * * * *